(12) United States Patent
Velschow et al.

(10) Patent No.: US 10,064,575 B2
(45) Date of Patent: Sep. 4, 2018

(54) MULTI LUMEN CATHETER

(71) Applicant: Fluisense ApS, Allerød (DK)

(72) Inventors: Sten Velschow, Vedbæk (DK); Henrik Harboe, Holte (DK); Martin Toft Madsen, København Ø (DK)

(73) Assignee: Fluisense ApS, Allerød (DK)

( * ) Notice: Subject to any disclaimer, the term of this patent is extended or adjusted under 35 U.S.C. 154(b) by 129 days.

(21) Appl. No.: 14/423,905

(22) PCT Filed: Apr. 16, 2014

(86) PCT No.: PCT/DK2014/050101
§ 371 (c)(1),
(2) Date: Feb. 25, 2015

(87) PCT Pub. No.: WO2014/169923
PCT Pub. Date: Oct. 23, 2014

(65) Prior Publication Data
US 2016/0022190 A1    Jan. 28, 2016

(30) Foreign Application Priority Data

Apr. 17, 2013    (DK) .................................. 2013 70217

(51) Int. Cl.
*A61B 5/15* (2006.01)
*A61M 25/00* (2006.01)
*A61B 5/155* (2006.01)

(52) U.S. Cl.
CPC .... *A61B 5/150992* (2013.01); *A61B 5/15003* (2013.01); *A61B 5/155* (2013.01);
(Continued)

(58) Field of Classification Search
CPC ...... A61M 25/0071; A61M 2025/0073; A61M 25/0009; A61M 25/0015; A61B 5/150992;
(Continued)

(56) References Cited

U.S. PATENT DOCUMENTS 2,804,075 A    8/1957    Borden
4,069,814 A    1/1978    Clemens
(Continued)

FOREIGN PATENT DOCUMENTS

EP    0107810 A1    5/1984
JP    H03505821 A    12/1991
(Continued)

*Primary Examiner* — Theodore Stigell
(74) *Attorney, Agent, or Firm* — Dinsmore & Shohl LLP

(57) ABSTRACT

A multi lumen catheter comprising a proximal end and distal end said catheter further comprising; a first lumen for a first fluid said first lumen having a first proximal opening and a first distal opening for receiving a fluid, second lumen for a second fluid said second lumen having a second proximal opening and a second distal opening for delivering a second fluid, a third lumen having a third proximal opening and a third distal opening, wherein the first distal opening is arranged with respect to the second distal opening so that when in use at least part of the first fluid which enters the first lumen through the first distal opening has passed across the second distal opening such that the first fluid which enters the first lumen comprise at least a part of the second fluid.

8 Claims, 4 Drawing Sheets

(52) U.S. Cl.
CPC ... *A61B 5/150755* (2013.01); *A61M 25/0009* (2013.01); *A61M 25/0015* (2013.01); *A61M 25/0071* (2013.01); *A61M 2025/0073* (2013.01)

(58) Field of Classification Search
CPC .............. A61B 5/155; A61B 5/150755; A61B 5/15003
See application file for complete search history.

(56) References Cited

U.S. PATENT DOCUMENTS

| | | | |
|---|---|---|---|
| 4,280,496 A | | 7/1981 | Van Baelen |
| 5,097,834 A | * | 3/1992 | Skrabal .............. A61B 5/14525 128/DIG. 13 |
| 5,221,255 A | | 6/1993 | Mahurkar et al. |
| 5,403,291 A | | 4/1995 | Abrahamson |
| 7,744,585 B2 | * | 6/2010 | Carrillo, Jr. ....... A61M 25/0029 604/523 |

FOREIGN PATENT DOCUMENTS

| | | |
|---|---|---|
| JP | 2000354634 A | 12/2000 |
| WO | 2006002192 A2 | 1/2006 |

* cited by examiner

MULTI LUMEN CATHETER

CROSS REFERENCE TO RELATED APPLICATIONS

This application is the U.S. national phase of No. PCT/DK2014/050101, filed Apr. 16, 2014, which claims priority to Denmark application No. PA 2013 70217, filed Apr. 17, 2013, the contents of both of which are incorporated herein in their entirety.

FIELD OF INVENTION

The invention relates to a catheter with at least three lumens.

BACKGROUND OF THE INVENTION

In biomedical research monitoring processes in living organisms is a constant focus.

Extracting blood or other body fluids from patients in order to diagnose disease states or monitor physiological conditions have applications in both intensive care hospital medicine, managing disease and interventions and in research.

Methods to monitor contents of analytes in blood generally involve accessing the circulation of the patient through a catheter venflon needle or other means.

The most common method is to extract a sample using a needle and vacuum tube whenever a blood parameter needs to be evaluated.

For many blood constituents this approach is sufficient especially where the concentration of blood analytes are fairly stable and only infrequent samples need be taken.

For more labile blood constituents, such as glucose, metabolic markers, hormones and other signalling molecules such as adrenaline and cortisol the concentrations may change rapidly within a short time frame and may even be directly influenced by the sampling procedure itself.

If blood concentration of these constituents are to be frequently determined either frequent manual blood samples must be taken or an automatic sampling system used.

Where samples must be taken continuously or at relatively small intervals the catheter can advantageously be inserted permanently into the vessel however problems may arise due to clogging of the lumen and/or opening of the catheter or any attached devices.

SUMMARY OF THE INVENTION

In a first aspect the present invention may be regarded as providing a catheter which enables continuous or periodic sampling of blood from a vessel.

In a second aspect the present invention may be regarded as providing a catheter which enables a continuous addition of an additive.

In a second aspect the present invention may be regarded as providing a catheter which enables the return of non-used blood to the vessel.

These and further advantages are provided by the present invention by a multi-lumen catheter comprising a proximal end (for connection with device) and distal end (for insertion in subject such as a human or animal) said catheter further comprising a first lumen for a first fluid said first lumen having a first proximal opening and a first distal opening for receiving a fluid, second lumen for a second fluid said second lumen having a second proximal opening and a second distal opening for delivering a second fluid, a third lumen having a third proximal opening and a third distal opening, wherein the first distal opening is arranged with respect to the second distal opening so that when in use at least part of the first fluid which enters the first lumen through the first distal opening has passed across the second distal opening such that the first fluid which enters the first lumen comprise at least a part of the second fluid.

Thus the fluid entering through the first distal opening and flowing through the first lumen is admixed with the second fluid (e.g. an additive) provided via the second lumen and out through the second distal opening.

If the first fluid is blood and the second fluid contains an anticoagulant the present catheter advantageously can be used for continuous and/or periodic blood sampling.

The first and second distal opening can be positioned in various ways with respect to each other as long as it is ensured that the first fluid which is sucked into the first lumen through the first distal opening passed the second distal opening through which the second fluid is expelled so that the first fluid is admixed with second fluid before being sucked into the first lumen.

Through the third lumen with a third proximal opening and a third distal opening a third fluid can be delivered or retrieved through the catheter. For example, the catheter can be used to obtain continuous or periodical blood samples through the first lumen, from blood a vessel in a body e.g. a human or an animal body into which the catheter is inserted, and into a test device which test/store part of the blood and return the remaining blood to the blood vessel through the third lumen.

When drawing samples from a blood vessel from an animal it is advantageous to be able to return unused blood to the animal as it will minimise the physiological effect which is caused by drawing blood.

The first fluid can be sucked into the first lumen constantly or in intervals without blood is clogging in the first distal opening and/or first lumen as blood in this region is admixed with the second fluid.

Thus the present invention is enabling the process of repeatedly, periodically and/or continuously extracting volumes of blood preferably very small volumes of blood or other bodily fluids automatically from a subject with minimal impact on the subject. The fluid is preferably extracted through optimized catheters preferably very small diameter catheters according to the present invention.

Blood has a strong propensity for coagulating on contact with basically any surface which is not endothelial lining of the blood vessels. This effect is related to the volume of blood in contact with a foreign surface, the flow speed, and the laminar nature of the flow. Thus a tube with a larger inner diameter will have less procoagulant effect than a tube with a smaller diameter, and the smaller diameter tube will clot and become obstructed before the larger diameter and a tube with lower flow speed will tend to clot and become obstructed before a similar tube with larger diameter.

In animals such as dogs and pigs the blood normally clots much faster than in humans.

Clotting and obstruction of catheters frequently happen at the very tip of the catheter or by the formation of clots in the vessel in the vicinity of the catheter tip.

Thus the principle of the invention is to generate a shielding coat of anticoagulant fluid around the first inlet, and when a first fluid is withdrawn through the catheter to mix with the first fluid with a second fluid in an optimal ratio, while also protecting the inner surface of the first fluid containing tubing from the blood. The highly laminar flow of fluids in small diameter tubing enhances this protective effect of the anticoagulant solution.

For example the first distal opening and the second distal opening connects to a common distal channel whereby the passage of the blood to the first distal opening is narrowly restricted thus providing full control of the mix between first and second fluid as well as it is ensured that the first distal opening is surrounded with the second fluid even when no fluid is withdrawn through the first distal opening.

The first distal opening and the second distal opening are arranged in a distal surface of the catheter whereby good flow conditions around the first and second distal opening is ensured when the catheter is inserted in a blood vessel.

The first and/or second distal opening can have various shapes and mutual configurations arranged to ensure optimal flow conditions in and especially around the first and second distal opening, for example the second distal opening at least partly encircles the first distal opening.

The second lumen can also be split in two parts e.g. forming two semi circles together encircling the first lumen.

The first and second opening can be flush i.e. in the same plane with e.g. the distal surface or the first and second distal opening can be off set with respect to each other and with respect to the distal end surface. Adjusting the mutual position of the first and second distal opening influences the flow conditions around at least the first and second opening.

The second fluid provided via the second lumen can be administered in regulated doses ensuring that the blood sucked into the first lumen does not clog but at the same is in a dose low enough to allow the remaining part of the blood sample to be returned to the vessel without any risk to the body of the animal or human from which the blood sample is drawn.

Advantageously the third distal opening is arranged downstream with respect to the first distal opening when the catheter is inserted in e.g. a blood vessel with flow to ensure that the first fluid sucked in through the first distal opening is not intermixed with the third fluid delivered back into the vessel through the third distal opening.

If the distal surface is cut at least at one an angle with respect to the longitudinal direction of the catheter it is possible to arrange the first, second and third distal opening with respect to each other in various advantageous configurations as will be discussed below.

The smaller the diameter of the catheter is the less discomfort to the subject. Larger catheters need larger incisions in the skin to reach the vessels, resulting in larger wounds and more tissue damage. A smaller catheter will affect a smaller volume of tissue and cause less inflammation.

Preferably the total outer diameter of the catheter with two or three lumens is 2 mm, 1.5 mm, 1.15 mm or less preferably to enable the catheter to be mounted through an 18 G needle, catheter, venflon or alternative means.

Preferably the diameter of the first, second and/or third lumen is chosen to have relative diameters in a mutual relationship which ensures that the third fluid through the third lumen has a higher flow velocity than the blood coming in through the first lumen, thus being propelled away from the tip to avoid being re-sampled through the first lumen. Preferably the largest diameter of the three lumens is less than 1 mm.

Preferably the diameter of the second lumen is the largest. Preferably the diameter of the third lumen is the smallest.

Preferably the diameter of the first, second and/or third lumen is approximately 0.3 mm, 0.6 mm and/or 0.1 mm in order to ensure that returning blood through third lumen has a higher flow velocity than the blood coming in through the first lumen, thus being propelled away from the tip to avoid being re-sampled through the first lumen.

The present invention also relates to a method for providing a labelling agent to a fluid retrieved by a multi lumen catheter as described herein, comprising the steps of;
  providing a second fluid through a second distal opening said second fluid comprising at least a labelling agent; and
  withdrawing a first fluid mixed with at least part of the second fluid through a first distal opening.

Thus the first fluid is mixed with the second fluid and thereby with the labelling agent which means that the labelling agent can be detected in subsequent analysis of the first fluid. Preferably the multi lumen catheter is a multi-lumen catheter as described herein.

If the labelling agent is a marker for providing a normal in analysis of the first fluid it is possible to normalize results in the subsequent analysis. I.e. if the relative content of the labelling agent in the first fluid is known the labelling agent can be used as an internal standard to determine the sample volume in later analysis. The analyses may for example be mass spectrometry (MS), Liquid Chromatography LC, LC/MS, High Power Liquid Chromatography (HPLC), HPLC/MS, MS/MS, LC/MS/MS, HPLC/UV, ELISA, RIA or any other quantitative or semi-quantitative analysis method.

The present invention provides a catheter enabling an automated blood sampling from a subject at any time point over the course of the day, unnoticed and without causing risk to the subject. The blood withdrawn can be prevented from coagulating in the tubing, in the device itself and at the site of extraction and the coagulant properties of the subjects circulating blood is not affected. Further the extracted amount can be so small as not to impact the subject's physiology even over extended periods of continuous sampling. In order to extract small volumes, it necessary that the diameters of the lumens of the catheter preferably are small.

Infusion of a fluid through second lumen ending within first lumen or around first lumen has several advantages:
  Delivers highest concentration of anticoagulant where it is most needed.
  Enables sampling with or without addition of anticoagulant solution.
  Makes use of flushing fluid for blood path unnecessary.
  Makes reversing flow in blood path unnecessary.
  No flushing of anticoagulant fluid through blood passageway.

Thus the present invention makes it possible to:
  Use a small diameter tubing or catheter in the body.
  Access peripheral venous circulation.
  Prevent clotting of the catheter tip, distal openings and catheter lumens.
  Cause minimal tissue damage during mounting.
  Infuse no systemic anticoagulants.
  Function in a robust fashion without the need of operator interaction after mounting.
  Infuse minimal amounts of fluid.
  Extract blood samples accurately representing the circulating blood in the body at the time of sampling.

When producing, connecting and/or handling a multi-lumen catheter of small dimensions such as the present invention it can be difficult to connect all lumens in the proximal end to a device, connector and/or tubing while ensuring that each lumen is separate, that the connection does not leak.

Connecting a multi lumen catheter where the lumens are not circular in cross section, which is the situation for several embodiments of the present invention, is further complicated by the fact that that the non-circular lumen will typically need to be converted into a circular lumen for easy connection in the proximal end.

The present application also relates to a method of connecting a multi-lumen catheter.

According to the method for connecting the catheter typically a core is placed in the lumen and a connection is cast or molded over the core which is subsequently removed.

If however the catheter lumen is oval or have more complicated shapes, and the core is circular, casting material will enter the lumen of the catheter and may later dislodge and be of risk to a patient or block flow through the catheter.

In the present invention a novel method for connecting the proximal ends of non-circular lumens of a multi lumen catheter is disclosed.

The catheter is cut in an oblique fashion to expose the lumens along the length of the cut. The larger the angle of the cut the further apart the lumens will present themselves.

A soft round core made from silver or tinned copper, or from teflon coated copper or other flexible material is inserted into each of the lumens. The soft cores can be bent at an angle up 90 degrees to the catheter, to separate the lumens to a maximal extent. The proximal end is then heated to a temperature that renders the catheter material soft and just below melting, and then a pressure is applied along the length of the inserted cores, so the cut is pressed closed around the cores where they enter the catheter.

The catheter proximal end can then be overmolded by injection molding or other molding method with a second material to enclose the cores and create fixture for further processing.

After cooling the cores are removed and each lumen can be easily accessed.

EXAMPLE

In a simple form a catheter for continuous access to the circulation has a distal and a proximal end and comprises a minimum of three lumens where the first lumen is proximally connected to a pumping means for drawing a first fluid from the circulation through the first lumen of the catheter. The second lumen is proximally connected to a fluid reservoir containing a second fluid and a means for infusing the second fluid. The third lumen returns at least part of the first fluid to the circulation.

The second lumen fully or partially envelopes the first lumen and for example the longitudinal distance between the ends of the two lumens i.e. first and second distal opening are between 0 and 1 mm or between 0 and 1.5 times the diameter of the outer lumen.

An anticoagulant fluid or flushing fluid is constantly infused through the second lumen at a flow rate of between 0.01 to 5 μl/s (microliters per second) in a way so as to let the anticoagulant fluid envelop the opening of the first lumen in the blood stream.

If no blood is sampled the infusion of anticoagulant fluid based on Sodium Citrate is preferably done at a flow rate between 0.05 to 2 μl/s, preferably 0.1 μl/s in order to ensure that the lumens of the catheter is kept from clogging. It may also be preferable to circulate blood through the first lumen and return it through the third lumen in a relatively low flow rate between 10 and 100 nl/s (nanoliter per second), preferably, 50 nl/s, in order to ensure that no clogging occurs in the system.

If blood is continually or periodically sampled the flow rate of the blood must be set so as to ensure that a suitable mixing ratio of blood and anticoagulant takes place. For citrate solutions (anticoagulant) this may e.g. be in the range of 1:8 to 1:15 depending on the citrate concentrations in the anticoagulant fluid. Preferably, the flow rate of the first fluid, when sampling, is between 0.1 and 5 μl/s, preferably 1 μl/s.

The enveloping in the above example as well as in other embodiments of the present invention effect can be generated by any of the following physical designs of the catheter and especially the catheter tip:

1. By letting the First and second lumen exit the catheter tip alongside each other.
2. As 1 where the wall separating the two lumens is recessed forming a cavity where first fluid and second fluid can mix.
3. As 1 where the second lumen fully or partially envelopes the first lumen.
4. As in 3 where the wall separating the lumens is recessed.
5. By letting the first lumen open into the second lumen and the second into the bloodstream: When no sample is being extracted the second fluid will flush the inlet of the catheter and prevent clotting. When the first fluid is being extracted into the first lumen it will pass the second lumen and be mixed with second fluid before entering the first lumen proper.

The second fluid in form of an anticoagulant solution can contain citrate as the active $Ca^{2+}$ chelating substance, but other anticoagulants such as heparin or LMW heparin, EDTA can be used.

Citrate has the specific advantage to many other anticoagulants that it is very quickly metabolised in the body and that its effects will be very local to the infusion site i.e. at the second distal opening.

DESCRIPTION OF THE DRAWINGS

The invention will in the following be described in greater detail with reference to the accompanying drawings.

DETAILED DESCRIPTION OF THE INVENTION

Figure 1:
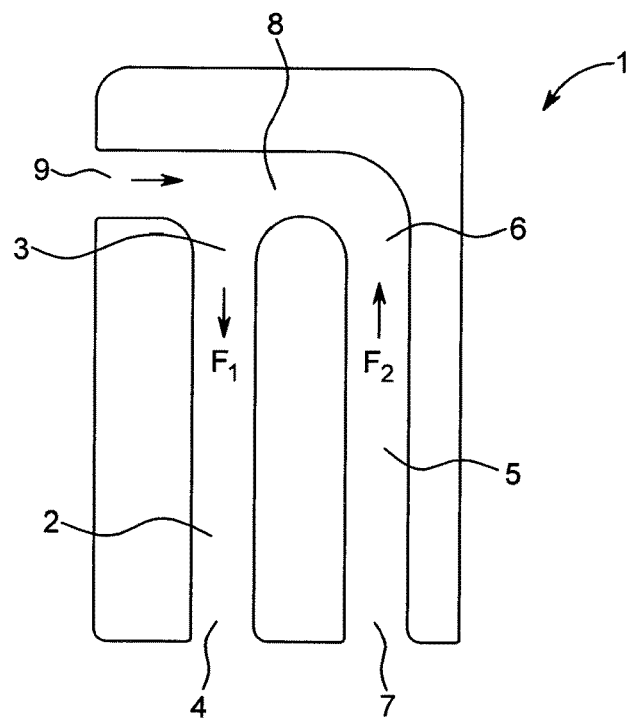
FIG. 1 a schematic view of a two lumen catheter

FIG. 1 shows a catheter 1 not forming part of the present invention. The catheter 1 comprises a first lumen 2 having a first distal opening 3, a first proximal opening 4 and a second lumen 5 having a second distal opening 6 and a second proximal opening 7.

The first and the second lumen run parallel along the longitudinal direction of the catheter. In FIG. 1 the catheter is shown in a short version however most embodiments are significantly longer than wide.

In FIG. 1 the first and second distal opening connects the first and second lumens respectively with a common channel 8 having a common opening 9.

The proximal end of the catheter is arranged to be attached to at least one pump means for withdrawing the first fluid and providing the second fluid.

The distal end is arranged to be inserted into e.g. a blood vessel from where the sample(s) are to be withdrawn.

Figure 2:
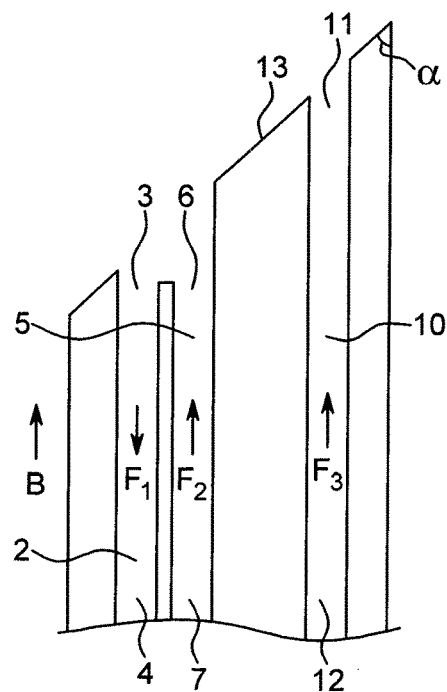
FIG. 2 a schematic view of a three lumen catheter according to the present

The embodiment shown in FIG. 2 comprises the features of the catheter of FIG. 1 and further comprises a third lumen 10 having third distal opening 11 and a third proximal opening 12. The catheter 1 further comprises a distal surface 13 cut at an angle α with respect to the longitudinal direction of the catheter.

The flow direction in each lumen is indicated by arrows F1, F2, and F3 respectively. The flow direction of the fluid in the vessel into which the catheter is inserted is indicated by arrow B.

It is seen that in the first lumen the fluid flows from the distal end towards the proximal end. In the second and third lumen the fluids flow towards the distal end from the proximal end.

Figure 3:
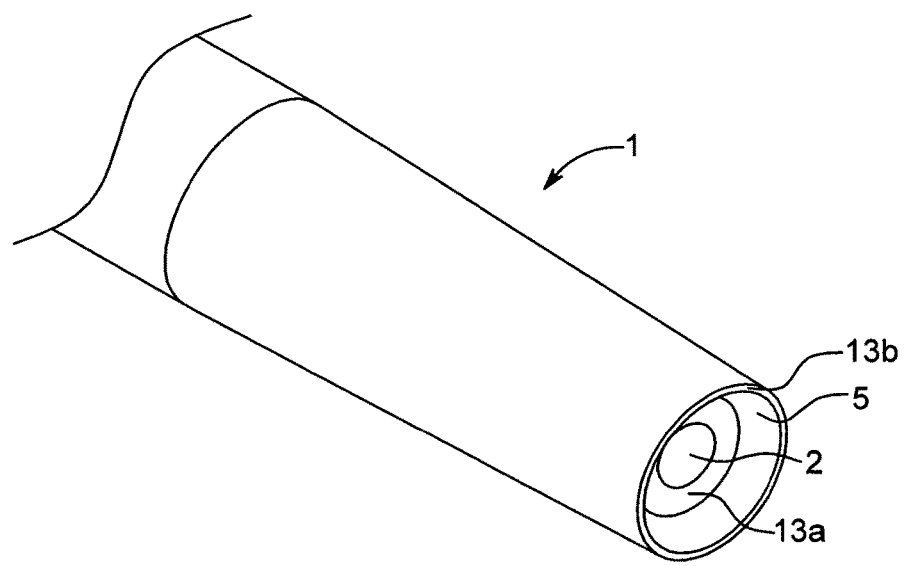
FIG. 3 a schematic view of an alternative two lumen catheter according to the present invention FIG. 4 a schematic view of a two catheter ends FIG. 5 a schematic view of various catheter arrangements according to the present invention FIG. 6 a schematic view of part of the process for connecting a catheter according to the present invention FIG. 7 a catheter connected to a connector.

FIG. 3 shows the distal end of an alternative two-lumen catheter according to the present invention wherein the first and second lumens are arranged as concentric circular lumens.

The distal end of the catheter is slightly tapered to enable a less invasive insertion in the test subject.

Figure 4A:
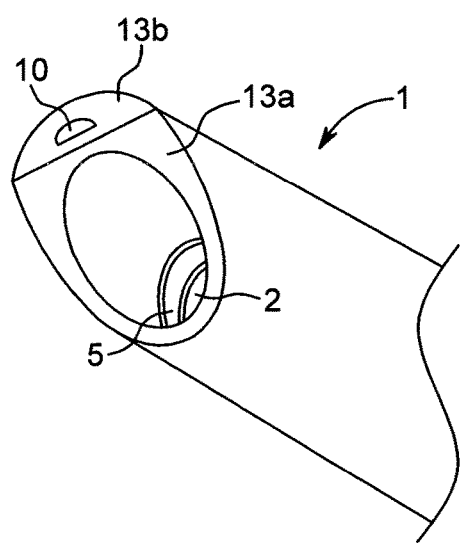
Figure 4B:
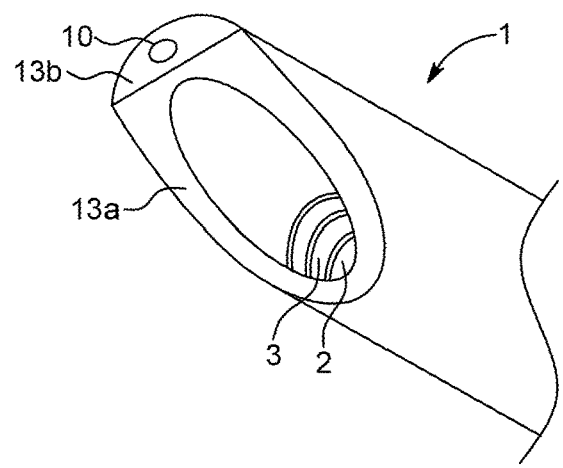

FIGS. 4a and 4b shows two alternative embodiments of catheters 1 with three lumens. In FIGS. 4a and 4b the end surface is cut to provide two end surfaces 13a and 13b at two different angels with respect to the longitudinal direction of the catheter. The angels of the cuts in the two embodiments of FIG. 4 are different so that the distal end surface of FIG. 4a is less inclined that the end surface of FIG. 4b whereby the cross sectional area of the opening in 4b is larger than the corresponding opening in 4a. Also the distance between the distal openings is affected by the angle of the cut.

The first end surface 13a has the first and second opening recessed into it and the second end surface 13b comprises the third distal opening so that when the catheter is inserted into a blood vessel the third distal opening is downs stream compared to the first and second distal opening.

Figure 5:
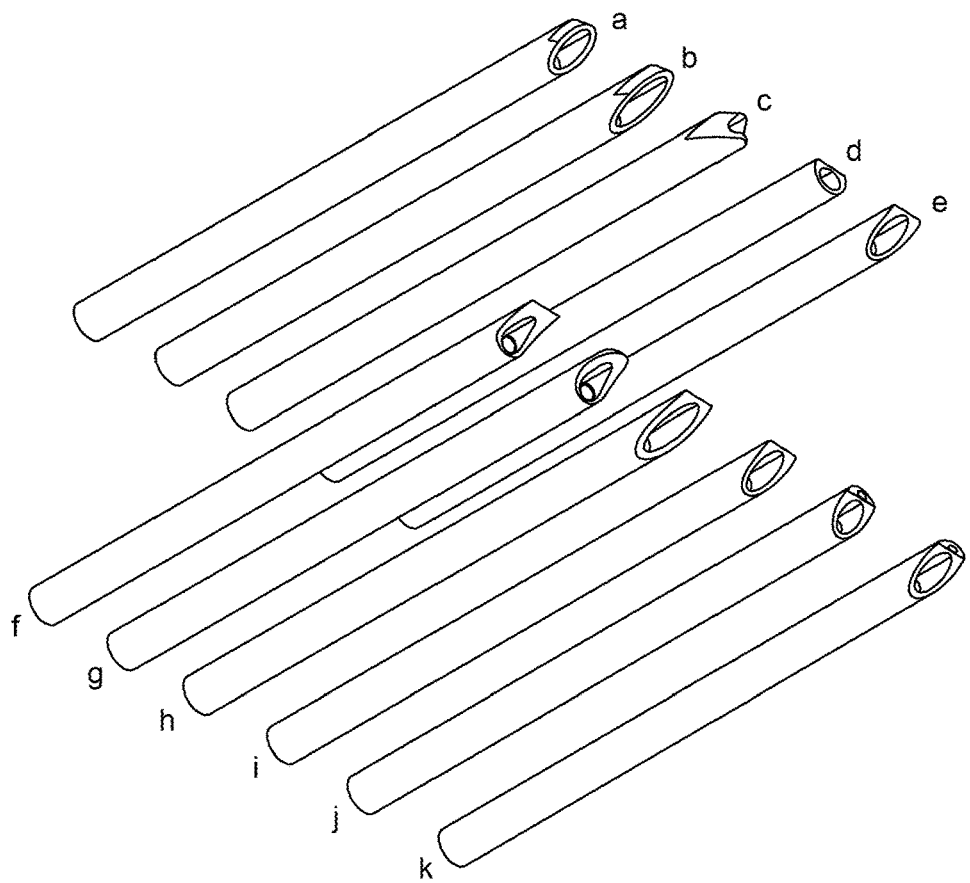

FIG. 5 shows eleven different embodiments a-k of catheters according to the present invention. Each catheter is arranged with a specific design of the end with one or more end surfaces arranged to obtain specialized flow conditions.

Figure 6:
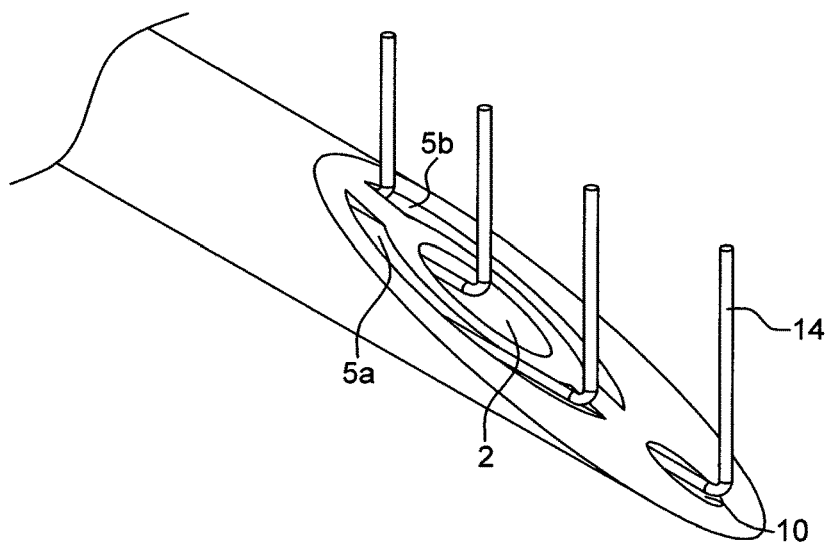

FIG. 6 illustrates a step in the method for attaching the proximal end of a multi lumen catheter to a connector. It is seen that four small cores 14 are inserted into the catheter one core in each lumen. From here the catheter end is ready to be heated, pressed and/or otherwise closed around the cores.

Figure 7:
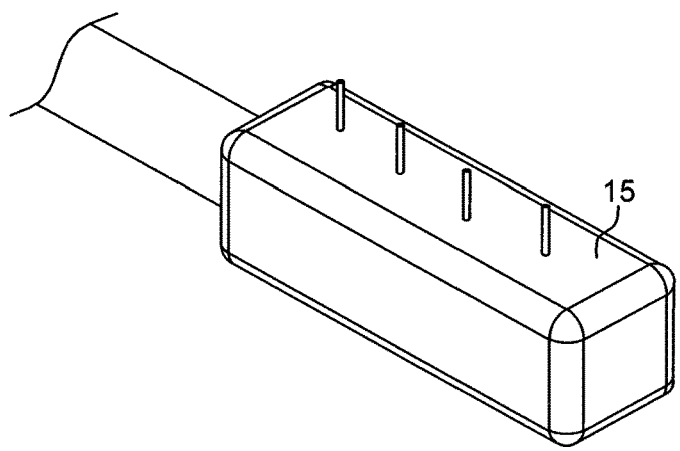

In FIG. 7 a housing has been moulded around the proximal end of the multi lumen catheter end and the inserted cores thereby forming a connector 15 enabling connection to one or more devices such as a blood sampling system.

Figure 8:
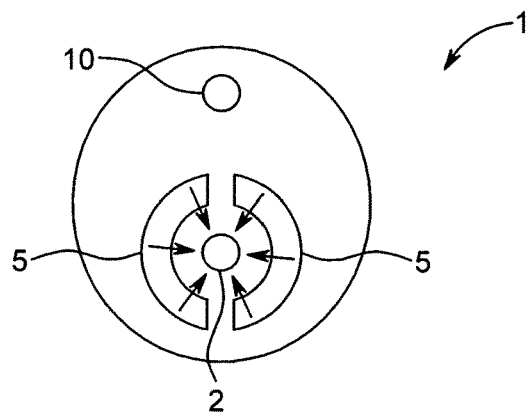
FIG. 8 a cross-sectional view of a catheter according to an embodiment of the invention

FIG. 8 is a cross sectional view of catheter with three lumens. The catheter has a diameter of approx. 1.2 mm. The first lumen 2 has a circular form with a diameter of approx. 0.36 mm. The second lumen 5 partly encircles the first lumen 2 and is split in two parts having a semi-circular form which has outer diameter of approx. 0.6 mm. The third lumen 10 is positioned such that no returning blood inters the first lumen 2. By use of the shown form of the second lumen 5 it can be ensured that the anticoagulant fluid or flushing fluid infused through the second lumen 5 flows towards the first lumen 2 from all sides, as illustrated by the arrows.

The invention claimed is:

1. A multi-lumen catheter comprising a proximal end and distal end, the distal end for insertion, said catheter further comprising;
   a first lumen for a first fluid, said first lumen having a first proximal opening and a first distal opening for receiving a fluid, wherein when in use, the first fluid flows from the first distal opening to the first proximal opening,
   a second lumen for a second fluid, said second lumen having a second proximal opening and a second distal opening for delivering a second fluid, wherein when in use, the second fluid flows from the second proximal opening to the second distal opening,
   a third lumen having a third proximal opening and a third distal opening for returning the first fluid to the distal end of the catheter, wherein the third distal opening is disposed closer towards the distal end of the catheter with respect to the first distal opening, and wherein when in use, the first fluid flows from the third proximal opening to the third distal opening so that the first fluid is returned at the distal end of the catheter,
   wherein the first distal opening is disposed alongside the second distal opening such that when in use at least part of the first fluid which enters the first lumen through the first distal opening has passed across the second distal opening such that the first fluid which enters the first lumen comprises at least a part of the second fluid.

2. A multi-lumen catheter according to claim 1, wherein the first distal opening and the second distal opening connects to a common distal channel.

3. A multi-lumen catheter according to claim 1, wherein the first distal opening and the second distal opening are arranged in a distal surface of the catheter.

4. A multi-lumen catheter according to claim 1, wherein the second distal opening at least partly encircles the first distal opening.

5. A multi-lumen catheter according to claim 1, wherein a surface of the distal end is cut at least at one an angle with respect to the longitudinal direction of the catheter.

6. A method for attaching a multi-lumen catheter of claim 1 to a device, comprising the steps of:
   cutting the proximal end of the catheter at an angle;
   inserting a pliable core in each lumen;
   heating the proximal end of the catheter to a temperature below the melting point of the catheter material;
   pressing the proximal end to seal tightly around the cores;
   molding a connector house around the proximal end and cores, and
   removing the cores.

7. A method for providing a labelling agent to a fluid retrieved by a multi-lumen catheter, comprising the steps of:
   providing the multi-lumen catheter of claim 1;
   providing the second fluid through the second distal opening, the second fluid comprising a labelling agent;
   withdrawing the first fluid mixed with at least part of the second fluid through the first distal opening.

8. A method according to claim 7, wherein the labelling agent is a marker for providing a normal in analysis of the first fluid.

* * * * *